(12) United States Patent
Nishimori et al.

(10) Patent No.: US 8,714,771 B2
(45) Date of Patent: May 6, 2014

(54) ILLUMINATION APPARATUS AND ILLUMINATION SYSTEM INCLUDING A PLURALITY OF ILLUMINATION APPARATUSES

(75) Inventors: Naoki Nishimori, Kyoto (JP); Akira Matsui, Kyoto (JP); Jun Ota, Kyoto (JP); Sayuki Nakada, Kyoto (JP); Rie Masuda, Kyoto (JP); Shingo Inazumi, Kyoto (JP)

(73) Assignee: OMRON Corporation, Kyoto-shi (JP)

( * ) Notice: Subject to any disclaimer, the term of this patent is extended or adjusted under 35 U.S.C. 154(b) by 0 days.

(21) Appl. No.: 13/880,801

(22) PCT Filed: Mar. 16, 2011

(86) PCT No.: PCT/JP2011/056228
§ 371 (c)(1),
(2), (4) Date: Apr. 22, 2013

(87) PCT Pub. No.: WO2012/066796
PCT Pub. Date: May 24, 2012

(65) Prior Publication Data
US 2013/0208472 A1    Aug. 15, 2013

(30) Foreign Application Priority Data
Nov. 19, 2010    (JP) .................................. 2010-258611

(51) Int. Cl.
*F21V 7/20*       (2006.01)
*F21V 21/00*      (2006.01)
*F21S 4/00*       (2006.01)

(52) U.S. Cl.
USPC . 362/217.12; 362/218; 362/294; 362/217.02; 362/217.16; 362/225; 362/244

(58) Field of Classification Search
USPC ................ 362/244, 294, 373, 217.01–217.17
See application file for complete search history.

(56) References Cited

U.S. PATENT DOCUMENTS 7,267,461 B2 *  9/2007  Kan et al. ...................... 362/373
7,857,482 B2 * 12/2010  Reo et al. ...................... 362/225
8,220,980 B2 *  7/2012  Gingrich, III ................. 362/612
(Continued)

FOREIGN PATENT DOCUMENTS

JP    2002-124119 A    4/2002
JP    2005-347279 A   12/2005
(Continued)

*Primary Examiner* — Mariceli Santiago
(74) *Attorney, Agent, or Firm* — Marvin A. Motsenbocker; Mots Law, PLLC

(57) ABSTRACT

An illumination apparatus includes an elongate chassis, a plurality of light emitting devices, a plurality of lenses, an elongate populated board, an elongate holding member, and a heat radiation member. The chassis includes a supporting portion supporting the opposite, longer-side ends of the populated board and a first engagement portion fitting and securing the holding member to the chassis. The holding member includes a plurality of second engagement portions fitting and securing each lens to the holding member and a resilient biasing portion resiliently biasing the longer-side ends of the populated board toward the supporting portion. The populated board is pinched and secured by the resilient biasing portion and the supporting portion and the heat radiation member is sandwiched and thus secured by the populated board and a bottom wall in contact with the populated board and the bottom wall.

9 Claims, 14 Drawing Sheets

(56) References Cited

U.S. PATENT DOCUMENTS

| | | | |
|---|---|---|---|
| 8,602,589 B2 * | 12/2013 | Sadeh et al. | 362/235 |
| 2003/0156416 A1 * | 8/2003 | Stopa et al. | 362/294 |
| 2009/0310354 A1 * | 12/2009 | Zampini et al. | 362/235 |
| 2012/0162974 A1 * | 6/2012 | Yu et al. | 362/218 |

FOREIGN PATENT DOCUMENTS

| | | |
|---|---|---|
| JP | 2007-59073 A | 3/2007 |
| JP | 2009-158144 A | 7/2009 |
| JP | 2010-27252 A | 2/2010 |
| WO | 2010/007835 A1 | 1/2010 |

* cited by examiner (A)

(B)

ILLUMINATION APPARATUS AND ILLUMINATION SYSTEM INCLUDING A PLURALITY OF ILLUMINATION APPARATUSES

TECHNICAL FIELD

The present invention relates to an illumination apparatus including a light emitting device as a light source, and an illumination system including a plurality of such illumination apparatuses, and in particular, an illumination apparatus and an illumination system including a plurality of such illumination apparatuses, that are employed in the field of art of image processing for exposing an object to light for shooting an image thereof.

BACKGROUND ART

Conventionally, various types of image processing techniques are utilized in the field of factory automation (FA) and the like. Typically, image processing technology is employed to shoot an image of an object to be inspected to obtain image data, and therefrom identify letters, markings and the like provided on the object, inspect whether the object has a damaged surface, register components to be assembled, and the like, and is introduced in various production facilities and the like.

To utilize such image processing technology, it is necessary to appropriately obtain an image shot of the object. Accordingly, image processing systems are often provided with an illumination apparatus to expose the object to light to ensure appropriate illumination intensity in shooting an image of the object. The illumination apparatus is generally equipped with a low power consumption and long life, high brightness light emitting device, such as a light emitting diode (LED), as a light source.

One such illumination apparatus attached to the above described image processing system is referred to as a bar/line type illumination apparatus. The bar/line type illumination apparatus emits light for illumination at a surface having a predetermined width and extending linearly, and has a structure having an elongate substrate populated with light emitting devices aligned in a line or a matrix.

The bar/line type illumination apparatus is assembled in structures, which are disclosed for example in Japanese Patent Laying Open No. 2007-059073 (Patent Literature 1) and WO2010/007835 (Patent Literature 2).

Patent Literature 1 discloses a bar/line type illumination apparatus including a casing having a bottom wall and a pair of sidewalls, a board disposed on the bottom wall and populated with light emitting devices, and a lens array thereon having a plurality of lens portions, and the lens array has an upper surface with an end fitted to an engagement hook of the pair of sidewalls of the casing so that the lens array and the casing sandwich and secure the populated board to provide an assembly structure.

Patent Literature 2 discloses a bar/line type illumination apparatus including a casing having a bottom wall and a pair of sidewalls, a resiliently compressive heat radiation member thereon, a board thereon populated with light emitting devices, and a lens array thereon having a plurality of lens portions, and the lens array has an engagement hook fitted in an engagement recess of the pair of sidewalls of the casing so that the lens array and the casing sandwich and secure the populated board and the heat radiation member to provide an assembly structure.

CITATION LIST

Patent Literature

[Patent Literature 1] Japanese Patent Laying-Open No. 2007-059073
[Patent Literature 2] WO2010/007835

SUMMARY OF INVENTION

Technical Problem

However, Patent Literature 1 or 2 discloses an assembly structure adopting a lens array structure having a plurality of lens portions integrated together via a base, and when this assembly structure is adopted, the elongate lens array will have significant variation in thickness in its longitudinal direction, and in molding, the lens array readily warps, which makes it difficult to assemble the lens array. Furthermore, if the warped lens array is secured to the casing by force, the lens array will also experience stress and as a result be impaired in reliability.

To allow a bar/line type illumination apparatus to reproduce illumination characteristics, such as irradiation intensity and focal distance, with precision, as designed, it is essential to provide positioning of the light emitting devices mounted on the board and the lens portions disposed to correspond to the light emitting devices (i.e., positioning within a plane parallel to the emission face (hereinafter referred to as "positioning within the x-y plane")) and positioning along the optical axis (hereinafter referred to as "positioning along the z axis") with precision. However, the elongate board may also warp due to its thermal history while it is being produced, and this will prevent precise positioning of the light emitting devices and the lens portions.

When seen from this viewpoint, Patent Literature 1 discloses an assembly structure such that the populated board pressed by the lens array is pressed to the bottom wall of the casing and thus secured, and accordingly, the board's warpage can be corrected and the board can thus be positioned along the z axis with precision, and furthermore, the lens array's projection is fitted in the populated board's recessed portion and accordingly, the array and the board can be positioned in the x-y plane with precision.

When the assembly structure of Patent Literature 1 is adopted, however, the populated board having warpage corrected causes reaction force, which will be exerted to the lens array, and a problem will thus remain in terms of reliability. Furthermore, if the populated board has large warpage, or if the populated board has large rigidity, or the like, securing the lens array to the casing will per se be difficult and a problem will also arise in terms of assemblability.

The assembly structure of Patent Literature 2 has the populated board and the casing with a resiliently compressive heat radiation member posed therebetween and the populated board pressed by the lens array is pressed to the heat radiation member and thus secured. The heat radiation member that compressively deforms will prevent the populated board from experiencing extreme stress and thus contribute to better assemblability and reliability, and furthermore, the lens array's projection is fitted in the populated board's recessed portion and accordingly, the array and the board can be positioned in the x-y plane with precision.

When the assembly structure of Patent Literature 2 is adopted, it is expected that the compressively deformed heat radiation member's resilient force corrects the populated board's warpage to some extent. In reality, however, the resilient force is significantly small and cannot correct the populated board's warpage, and if the populated board has large warpage, or if the populated board has large rigidity, in particular, the warpage will hardly be corrected and the populated board still cannot be positioned along the z axis with precision.

The conventional bar/line type illumination apparatus thus still has a room for improvement in its assembly structure in view of reliability, significantly precise positioning with a component's warpage taken into consideration, and the like.

The present invention has been made to overcome the above disadvantages, and it contemplates an illumination apparatus that allows a light emitting device and a lens portion to be positioned with precision, is excellent in assemblability, and is of high performance and significantly reliable, and an illumination system including a plurality of such illumination apparatuses.

Solution to Problem

The present invention provides an illumination apparatus including: an elongate casing; a plurality of light emitting devices serving as a light source; a plurality of lenses disposed to correspond to the plurality of light emitting devices; an elongate, populated board having a front surface and a back surface and populated at the front surface with the plurality of light emitting devices such that at least a portion of the plurality of light emitting devices are aligned in a longitudinal direction of the populated board; a holding member disposed opposite to the front surface of the populated board and holding the plurality of lenses; and a heat radiation member disposed along the populated board opposite to the back surface of the populated board. The casing includes: a bottom wall; a pair of sidewalls erected from a pair of opposite, longer-side ends of the bottom wall; a housing portion defined by the bottom wall and the pair of sidewalls and receiving the plurality of light emitting devices, the populated board, the plurality of lenses, the holding member and the heat radiation member therein; a pair of supporting portions projecting from the pair of sidewalls toward the housing portion and supporting a pair of opposite, longer-side ends of the populated board; and a pair of first engagement portions provided at the pair of sidewalls and fitting and securing the holding member to the casing. The holding member includes: a plurality of openings associated with the plurality of light emitting devices; a plurality of second engagement portions fitting and securing the plurality of lenses to the holding member in such a manner that the plurality of openings are covered; and a plurality of resilient biasing portions resiliently biasing the pair of longer-side ends of the populated board toward the pair of supporting portions. The populated board is pinched and thus secured by the plurality of resilient biasing portions and the pair of supporting portions, and the heat radiation member is sandwiched and thus secured by the populated board and the bottom wall in contact with the populated board and the bottom wall.

In the present illumination apparatus preferably the plurality of resilient biasing portions are each configured of a resiliently deformable beam and a projection provided on the beam at a major surface closer to the populated board and in that case preferably the projection has only a tip thereof abutting against the front surface of the populated board.

In the present illumination apparatus preferably the plurality of second engagement portions fit and secure the plurality of lenses to the holding member such that the plurality of lenses each have a portion abutting against a surface of the holding member opposite to the populated board.

In the present illumination apparatus, preferably the holding member further includes a plurality of columns projecting toward the bottom wall and preferably the populated board includes a plurality of through holes associated with the plurality of columns and penetrating the populated board from the front surface to the back surface, and preferably the plurality of columns are inserted through the plurality of through holes.

Preferably the present illumination apparatus further includes: a connection cable having one end connected to the populated board and the other end pulled out of the casing and thus externally connected; and a securing member for securing the connection cable to the casing. In that case, preferably the casing further includes a first closing member disposed at a position corresponding to one of a pair of opposite, shorter-side ends of the bottom wall to define the housing portion, and preferably the securing member is secured to the connection cable externally at a portion other than the ends and also fitted and secured to the first closing member.

In the present illumination apparatus preferably the casing further includes a second closing member that is detachably attachable to a position corresponding to the other of the opposite, shorter-side ends of the bottom wall and defines the housing portion when the second closing member is attached to the position.

In the present illumination apparatus preferably the plurality of light emitting devices, the plurality of lenses and the plurality of openings are all disposed in a longitudinal direction of the casing equally in pitch. In that case, preferably, of the plurality of openings, the opening closest to a longitudinal end of the holding member has a portion closest to the longitudinal end with a distance to the longitudinal end of ½ of a width of a bar of the holding member located between adjacent ones of the openings.

In the present illumination apparatus preferably the plurality of light emitting devices, the plurality of lenses, the populated board and the holding member together configure an elongate subassembly and in that case such subassemblies may be disposed in the casing implemented as a single member such that the subassemblies are aligned in a longitudinal direction of the casing.

The present invention provides an illumination system including more than one illumination apparatus described above, and the illumination apparatuses are aligned in a longitudinal direction of the casing and mutually coupled and thus secured together.

Advantageous Effects of Invention

The present invention can thus provide an illumination apparatus that allows a light emitting device and a lens portion to be positioned with precision, is excellent in assemblability, and is of high performance and significantly reliable, and an illumination system including a plurality of such illumination apparatuses.

DESCRIPTION OF EMBODIMENTS

Hereinafter, the present invention in embodiments will be described in detail with reference to the figures. In the following embodiments, identical or common components are identically denoted in the figures and will not be described repeatedly in detail.

First Embodiment

Figure 1:
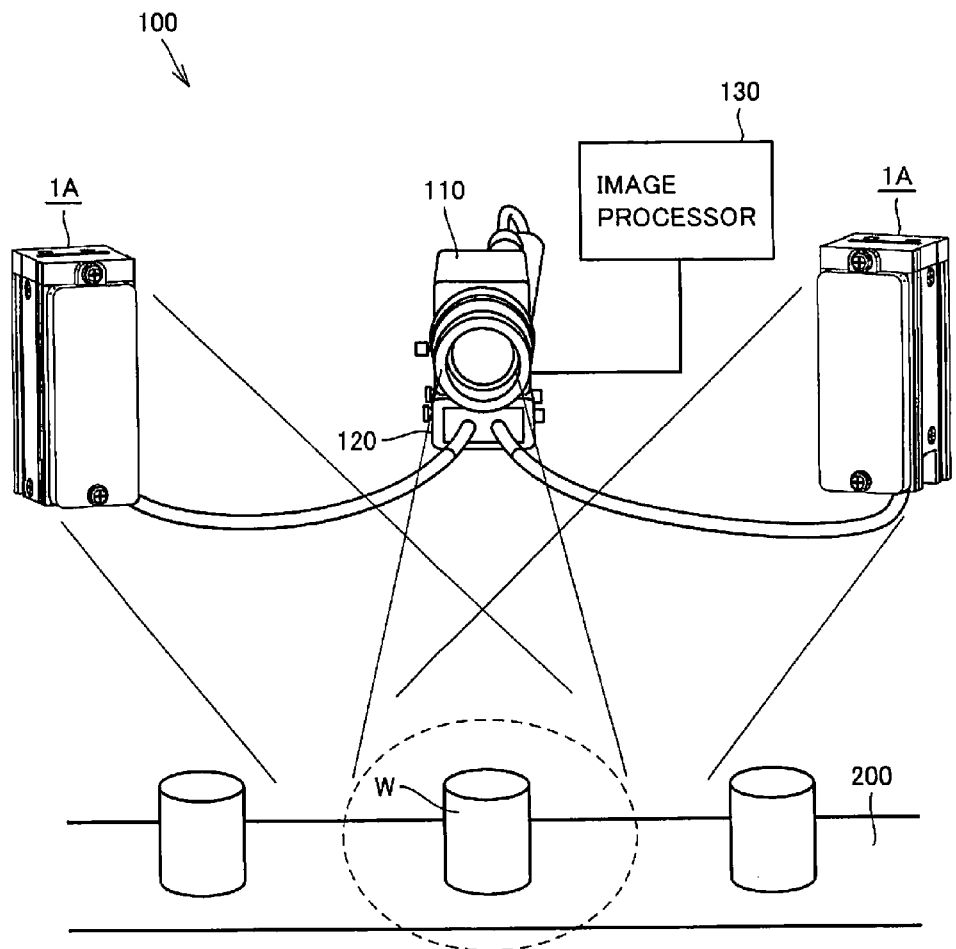
FIG. 1 is a schematic diagram showing an example in configuration of an image processing system equipped with an illumination apparatus in a first embodiment of the present invention.

FIG. 1 is a schematic diagram showing an example in configuration of an image processing system equipped with an illumination apparatus in a first embodiment of the present invention. Initially, before describing an illumination apparatus 1A in the present embodiment in detail, an example in configuration of an image processing system 100 equipped with illumination apparatus 1A will be described with reference to FIG. 1.

As shown in FIG. 1, for example, image processing system 100 is configured of a camera 110 for shooting an image, illumination apparatus 1A for illuminating a range of a field of view of camera 110 and its vicinity, a strobe light controller 120 as an illumination control device controlling an operation of illumination apparatus 1A, and an image processor 130 processing the image shot by camera 110.

Camera 110 is disposed such that its field of view has a range overlapping a path 200 transporting a workpiece W serving as an object to be shot to obtain an image thereof, and camera 110 is configured including a lens and/or a similar optical system, and in addition, a coupled charged device (CCD), a complementary metal oxide semiconductor (CMOS) sensor and/or a similar image pickup element. Note that preferably camera 110 is equipped with an electronic shutter mechanism to be able to shoot an image of a workpiece transported relatively fast.

When a workpiece detection sensor or the like (not shown) senses that workpiece W transported on transport path 200 has entered the range of the field of view of camera 110, camera 110 shoots an image of workpiece W, and outputs image data of the shot image to image processor 130. Alternatively, camera 110 may continuously be used to shoot an image of the range of the field of view and image processor 130 may extract selectively only an image including workpiece W.

Strobe light controller 120 is a device which drives illumination apparatus 1A in synchronization with camera 110 shooting an image, and has at least a function to feed illumination apparatus 1A with power, a function to control illumination apparatus 1A to time it, and a function to control illumination apparatus 1A in quantity of light (or a light modulating function). As has been described above, camera 110 is basically timed, as predetermined, to shoot an image of workpiece W, and illumination apparatus 1A is only required to emit light to the range of the field of view and its vicinity in this image shooting period for illumination. Accordingly, strobe light controller 120 normally drives illumination apparatus 1A intermittently in pulses.

Image processor 130 is a computer having an operation processing unit implemented as a central processing unit (CPU), a storage unit implemented as volatile memory, a hard disk and/or the like, a camera interface, and the like, and is connected to camera 110 and strobe light controller 120. Image processor 130 controls camera 110 and strobe light controller 120 to drive them to obtain image data of an image of workpiece W, and uses the obtained image data to perform various analyses.

Illumination apparatus 1A includes a light source in the form of a light emitting device emitting light to expose thereto the range of the field of view and its vicinity. Illumination apparatus 1A is connected to strobe light controller 120, and as has been set forth above, it is driven as controlled by strobe light controller 120. Normally, illumination apparatus 1A is secured in a vicinity of path 200 transporting workpiece W. Note that preferably a plurality of illumination apparatuses 1A are provided to surround the range of the field of view of camera 110 to prevent the shot image from including shadow.

Figure 2:
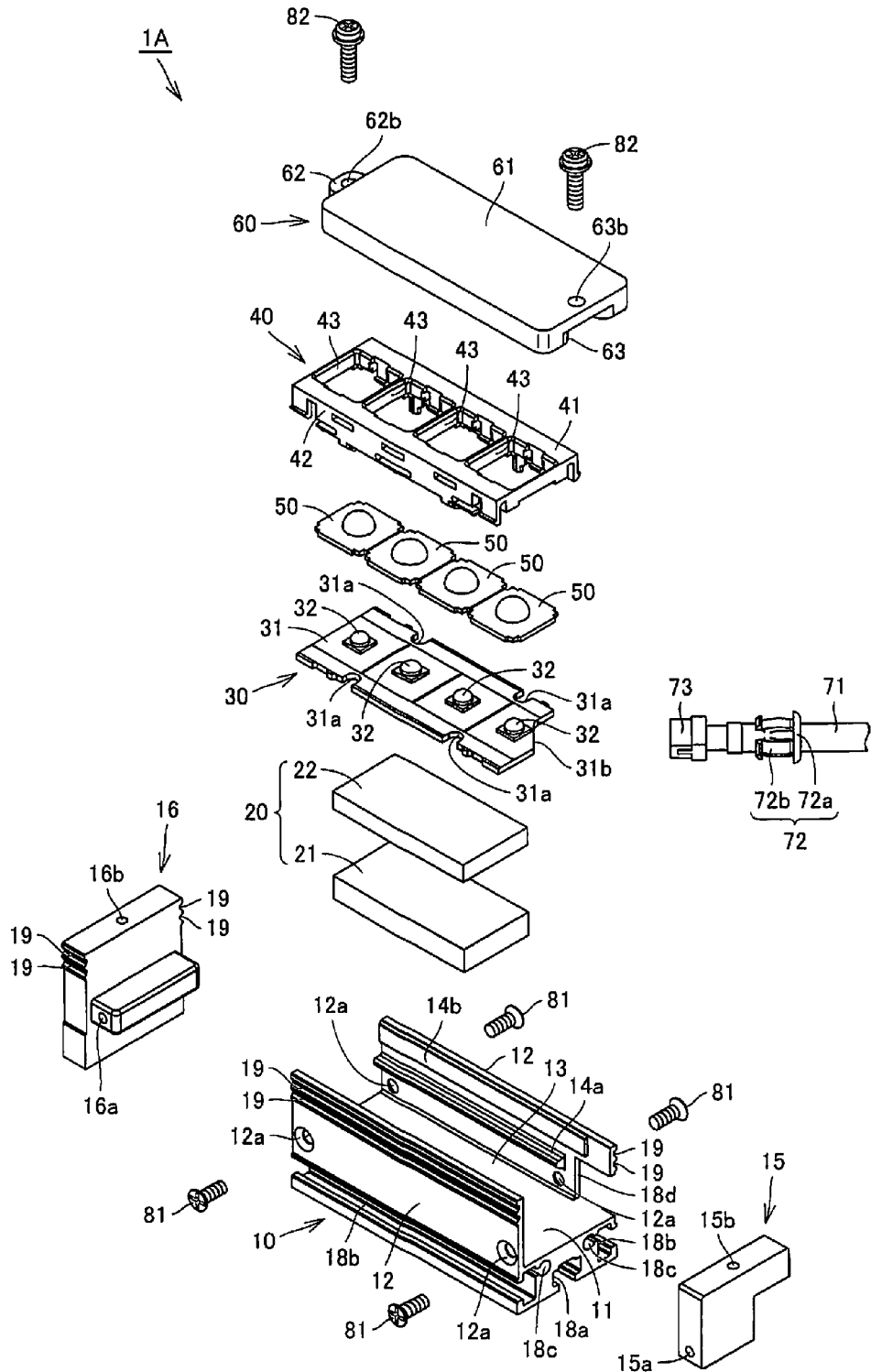
FIG. 2 is an exploded perspective view of the illumination apparatus in the first embodiment of the present invention.
Figure 3:
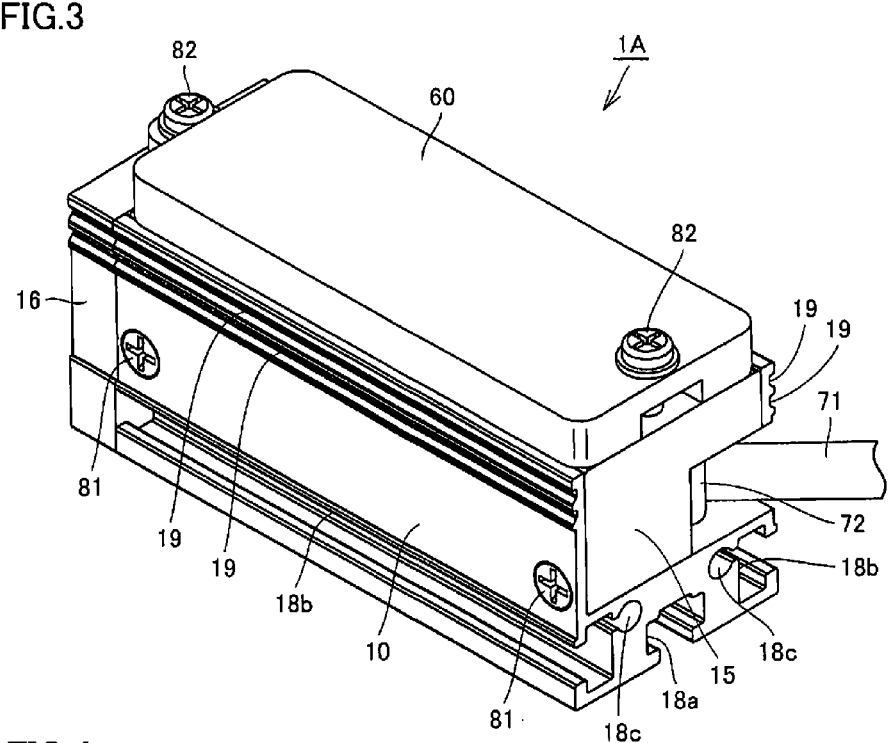
FIG. 3 is a perspective view of the illumination apparatus in the first embodiment of the present invention.
Figure 4:
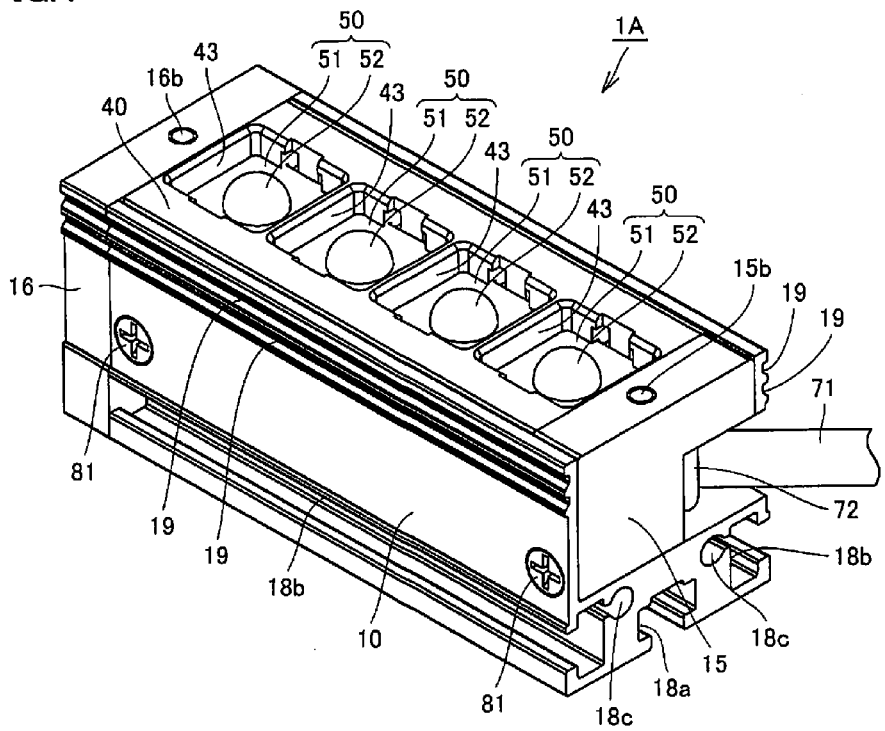
FIG. 4 is a perspective view of the illumination apparatus in the first embodiment of the present invention with a transparent cover removed.
Figure 5:
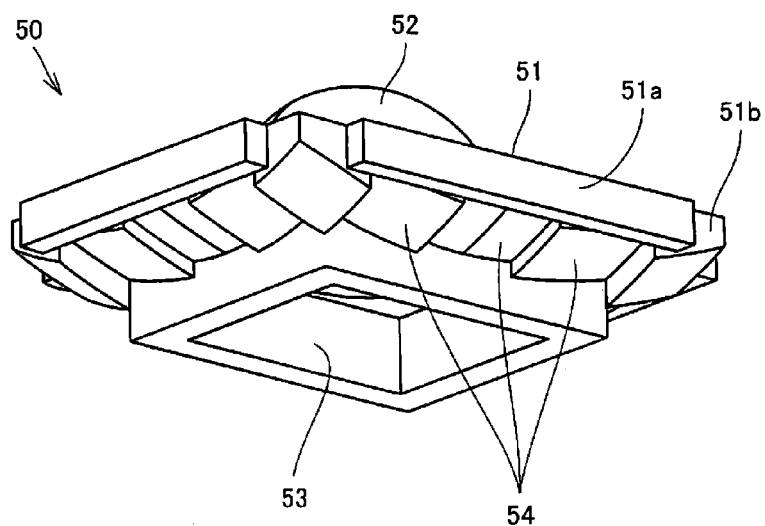
FIG. 5 is a perspective view of a lens of the illumination apparatus in the first embodiment of the present invention.
Figure 6:
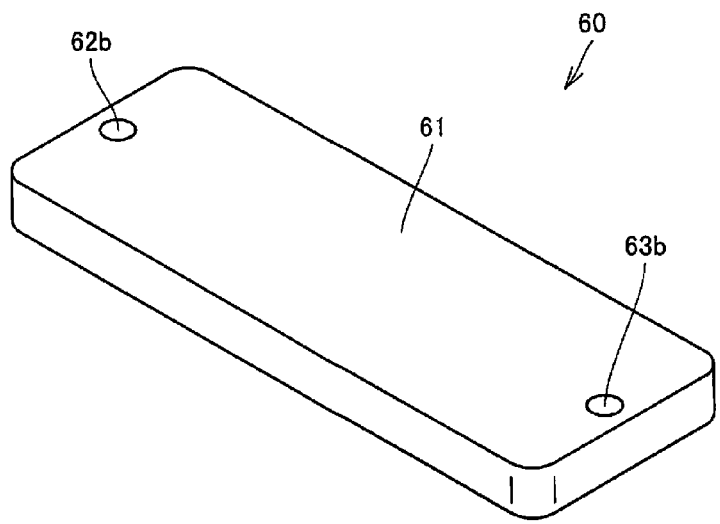
FIG. 6 is a perspective view showing another example of the transparent cover of the illumination apparatus in the first embodiment of the present invention.
Figure 7:
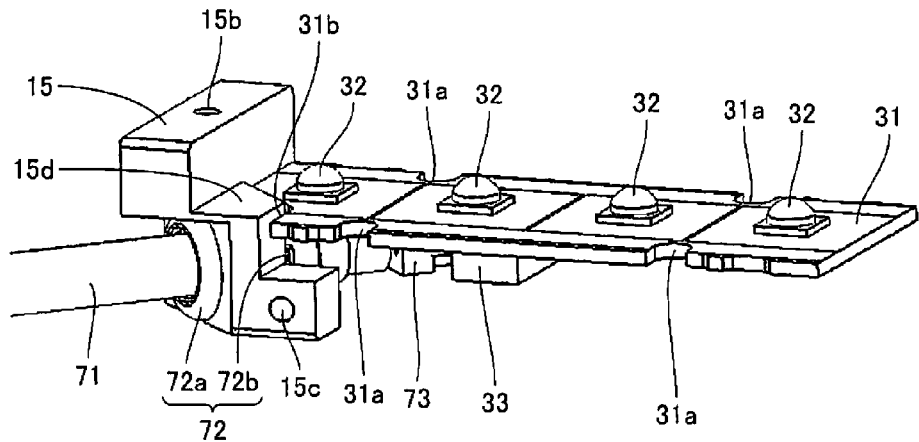
FIG. 7 is a perspective view of a main portion of the illumination apparatus in the first embodiment of the present invention.

FIG. 2 is an exploded perspective view of the illumination apparatus in the present embodiment and FIG. 3 is a perspective view after assembly. FIG. 4 is a perspective view of the illumination apparatus in the present embodiment without a transparent cover. FIG. 5 is a perspective view of a lens of the illumination apparatus in the present embodiment. FIG. 6 is a perspective view showing another example of the transparent cover of the illumination apparatus in the present embodiment. FIG. 7 is a perspective view of a main portion of the illumination apparatus in the present embodiment. Reference will be made to FIG. 2 to FIG. 7 to describe a schematic assembly structure of illumination apparatus 1A in the present embodiment, and its external appearance in structure after assembly.

As shown in FIG. 2 to FIG. 4, the present embodiment provides illumination apparatus 1A mainly including a chassis 10 as a casing, a first cover 15 as a first closing member and a second cover 16 as a second closing member, a pair of highly thermally conductive sheets 21 and 22 as a heat radiation member 20, a light source unit 30 including a populated board 31 and a plurality of light emitting devices 32 as a light source, a holding member 40, a plurality of lenses 50, a transparent cover 60, and a connection cable 71.

As shown in FIG. 2, chassis 10 is an elongate member which has a bottom wall 11 and a pair of sidewalls 12, and is formed for example with a metallic material serving as a source material, which undergoes extrusion, pultrusion or the like and is thus formed in one piece. The pair of sidewalls 12 erects from a pair of opposite, longer-side ends of bottom wall 11 generally in a rectangle as seen in a plane, and bottom wall 11 and the pair of sidewalls 12 define a housing portion 13.

Chassis 10 has the pair of sidewalls 12 with a pair of supporting portions 14a projecting from sidewalls 12 towards housing portion 13 and a pair of first engagement portions 14b. The pair of supporting portions 14a and the pair of first engagement portions 14b both extend in the longitudinal direction of chassis 10. The pair of supporting portions 14a is a part for supporting the longer-side ends of populated board 31, and the pair of first engagement portions 14b is a part for fitting and securing holding member 40. Note that the pair of first engagement portions 14b is configured by stepped surfaces positioned opposite to the bottom surface of chassis 10, and engages a first hook 45 (see FIG. 8, FIG. 9, and FIG. 11) serving as a portion provided at holding member 40 to be engaged, as will be described hereinafter.

As shown in FIG. 2 to FIG. 4, first cover 15 and second cover 16 are detachably attached to a position corresponding to a pair of opposite, shorter-side ends of bottom wall 11, and first and second covers 15 and 16 attached to chassis 10, and bottom wall 11 and the pair of sidewalls 12 together define housing portion 13.

Herein, first cover 15 is also a member receiving and holding connection cable 71 therethrough, and has a securing portion 15d (see FIG. 7) to which a cable holding member 72 attached to connection cable 71, as will be described later, is secured. First cover 15 is attached on chassis 10 to close one longitudinal end of chassis 10. In contrast, second cover 16 is attached to chassis 10 to close the other longitudinal end of chassis 10 by covering an axial end face of chassis 10 located at the other longitudinal end of chassis 10. Note that first cover 15 and second cover 16 are members formed with a resin material used as a source material and for example injection-molded.

Note that chassis 10 configuring the casing and second cover 16 are provided with a plurality of grooves 18a, 18b, and 18c for installing and securing illumination apparatus 1A, and a plurality of heat radiating grooves 19, extending in the longitudinal direction of chassis 10. Grooves 18a and 18b have an internal space expanding inside chassis 10 and capable of receiving a nut for bolting illumination apparatus 1A to a fixture or the like (not shown). Furthermore, groove 18c is round in cross section communicating with groove 18b, and can receive a screw for securing illumination apparatus 1A to a fixture or the like (not shown). Furthermore, the chassis 10 sidewall 12 is provided with a notch 18d at an end adjacent to securing portion 15d for pulling out connection cable 71 from a corner of the casing.

As shown in FIG. 2, chassis 10 has a plurality of screw holes 12a through the pair of sidewalls 12 at prescribed positions, and first and second covers 15 and 16 have side surfaces with screw holes 15a and 16a at prescribed positions to correspond to the plurality of screw holes 12a, respectively. Screw holes 12a, and 15a and 16a are provided to secure first cover 15 and second cover 16 to chassis 10, and each screw hole 12a and screw hole 15a/16a are registered and in that condition a fastening member, or a plurality of screws 81, is screwed thereinto to secure these members together.

Furthermore, first cover 15 and second cover 16 have upper surfaces with screw holes 15b and 16b at prescribed positions, respectively. Screw holes 15b and 16b are used to secure transparent cover 60 to the casing.

As shown in FIG. 2, housing portion 13 houses a pair of highly thermally conductive sheets 21 and 22, light source unit 30, holding member 40, and a plurality of lens 50, stacked in layers in this order.

The pair of highly thermally conductive sheets 21 and 22 configures heat radiation member 20 disposed at a back surface of populated board 31 of light source unit 30. More specifically, heat radiation member 20 is disposed at the back surface of populated board 31 of light source unit 30 to have an upper surface in contact with the back surface of populated board 31 and have a lower surface in contact with bottom wall 11 of chassis 10.

Furthermore, holding member 40 is disposed at a front surface of populated board 31 of light source unit 30, partially abutting against populated board 31, and the plurality of lens 50 are disposed at the front surface of populated board 31 of light source unit 30, with each lens attached to holding member 40.

The pair of highly thermally conductive sheets 21 and 22 is elongate insulating members having a predetermined thickness, and at least one of them is a compressively deformable member. Suitably, highly thermally conductive sheets 21 and 22 are silicon, acrylic or like resin sheets. Note that heat radiation member 20 radiates the heat generated by various electronic components, such as the light emitting devices mounted on board 31, a resistive element, and the like, and ideally it is preferable that it has sufficient elasticity and sufficient thickness to fit to a back surface of populated board 31 (also including an electronic component if it is mounted on populated board 31 at the back surface) and in that condition contact it. To bring heat radiation member 20 into sufficient contact with populated board 31, it is desirable that it has a thickness larger than the distance between bottom wall 11 and supporting portion 14a.

Populated board 31 is a flat elongate plate member, and configured as a rigid printed board represented by a glass epoxy board for example. Populated board 31 has a front surface and a back surface with wiring patterns and various electronic components are mounted on populated board 31 to form a circuit. In particular, populated board 31 has the front surface with a plurality of light emitting devices 32 mounted thereon aligned linearly in the longitudinal direction of populated board 31. Herein, the plurality of light emitting devices 32 are disposed in the longitudinal direction of populated board 31 equally in pitch.

Populated board 31 has the longer-side ends with a notch 31a at a prescribed position to serve as a portion penetrating from its front surface through to its back surface. Notch 31a is a part receiving and passing therethrough a column 46 (see FIG. 8, FIG. 9, and FIG. 12) of holding member 40 described later.

Furthermore, populated board 31 has four corners, of which a portion corresponding to that corner of the casing at which connection cable 71 is pulled out is provided with a notch 31b. Notch 31b is a part for forming a space in which first cover 15 has securing portion 15d disposed (see FIG. 7).

Furthermore, a connector 33 (see FIG. 7 and FIG. 9) is assembled at the back surface of populated board 31. Connector 33 is a part to which a connector 73 attached to a tip of connection cable 71 described later is connected.

Light emitting device 32 is a component that serves as a light source of illumination apparatus 1A, and can for example be an LED or the like. Light emitting device 32 can be various devices, such as a bullet type light emitting device, a surface mounted type chip light emitting device, and a bear chip, depending on the difference in geometry, how it is mounted, and the like. Note that, in the present embodiment, light emitting device 32 is a surface mounted type chip LED by way of example.

Holding member 40 is an elongate member having a base 41 and a pair of side plate portions 42, and is formed for example with a resin material serving as a source material, which is injection-molded or the like and thus formed. Base 41 is generally rectangular as seen in a plane, and the pair of side plate portions 42 erects from base 41 at a pair of opposite, longer-side ends. Base 41 has a plurality of openings 43 aligned at a prescribed position linearly in the longitudinal direction of holding member 40 to correspond to light emitting devices 32 mounted on board 31. Herein, the plurality of openings 43 are provided in the longitudinal direction of holding member 40 equally in pitch depending on the pitch of light emitting devices 32 disposed on board 31. Note that holding member 40 may not be an elongate one piece; rather, it may be divided such that each division corresponds to a single lens 50.

As shown in FIG. 2, FIG. 4, and FIG. 5, lens 50 is a member formed with a transparent resin material as a source material, which is injection-molded or the like and thus formed, and it has a base 51 and a lens portion 52. The plurality of lens 50 each has a single lens portion 52, and the plurality of lens 50 are associated with light emitting devices 32 mounted on board 31. Note that base 51 has peripheral side surfaces each provided with an ear 51a in association therewith. Ear 51a is a part for securing lens 50 to holding member 40, and is a part engaged by a second hook 44 of holding member 40 described later.

As shown in FIG. 5, lens 50 has lens portion 52 at one side, and a recessed portion 53 at an opposite side to accommodate light emitting device 32. Furthermore, base 51 at the opposite side has a plurality of reflection planes 54 each for a predetermined section. Light emitting device 32 accommodated in recessed portion 53 emits light, which has a major portion linearly guided to recessed portion 53 and emitted through lens portion 52 in a predetermined direction. On the other hand, of the remainder of the light, the light guided in a direction different from the optical axis is reflected by reflection plane 54. As a result, such lights are propagated in a varied direction and thus guided toward a plane in which lens portion 52 is formed (or a light emission face). Reflection plane 54 allows light emitted from light emitting device 32 to be emitted from the light emission face more efficiently.

The plurality of lens 50 are held by holding member 40 by being attached to holding member 40 so as to cover the plurality of openings 43 of holding member 40. Thus the plurality of lens 50 will be disposed in the longitudinal direction of holding member 40 equally in pitch, and will have their respective lens portions 52 also disposed in the longitudinal direction of holding member 40 equally in pitch.

As shown in FIG. 2 and FIG. 3, transparent cover 60 is a flat elongate plate member formed with a transparent resin material as a source material, which is injection-molded or the like and thus formed, and it has a diffusion plate portion 61, and a projection 62 provided at one longitudinal end of diffusion plate portion 61 and a recessed portion 63 at the other longitudinal end of diffusion plate portion 61. Diffusion plate portion 61 is a member receiving light from light emitting device 32 for diffusing the light to render it suitable for illumination.

Transparent cover 60 is attached to an upper surface of the casing so as to cover the casing's housing portion 13 having various components accommodated therein. Transparent cover 60 projection 62 and recessed portion 63 are provided with screw holes 62b and 63b, respectively, corresponding to screw holes 15b and 16b provided in first cover 15 and second cover 16. Screw holes 15b, 16b, 62b, 63b are used to secure transparent cover 60 to the casing, and screw holes 15b and 16b and screw holes 62b and 63b are registered and in that condition a fastening member in the form of a plurality of screws 82 is screwed thereinto to secure these members.

Herein, transparent cover 60 may be provided with an optical filter to selectively transmit only the light of a predetermined wavelength. Furthermore, transparent cover 60 may be a simple, elongate flat plate as shown in FIG. 6. Note that if it is not a requirement to diffuse the light emitted from the light emission face of lens 50, transparent cover 60 may not be attached to the casing (that is, the assembly may be used as shown in FIG. 4).

As shown in FIG. 2 to FIG. 4 and FIG. 7, connection cable 71 is used to provide electronic components mounted on populated board 31 and a circuit configured thereby with various transmission signals and power source, and has one end connected to populated board 31, and the other end to an external terminal (e.g., strobe light controller 120). Connection cable 71 is connected to populated board 31 electrically and physically by connecting connector 73 that is attached to a tip of connection cable 71 to connector 33 assembled to populated board 31. Connection cable 71 has a tip thereof inserted into the casing via an insertion hole of first cover 15 and is attached to first cover 15 via a securing member or cable holding member 72.

As shown in FIG. 2 and FIG. 7, cable holding member 72 has an annular abutting portion 72a surrounding connection cable 71 circumferentially, and a hook 72b erected from abutting portion 72a. Cable holding member 72 is secured to connection cable 71 externally at an intermediate position, and when it is assembled, it is fitted to securing portion 15d of first cover 15 (See FIG. 7). More specifically, abutting portion 72a abuts against an external surface of securing portion 15d and hook 72b is inserted into a through hole of securing portion 15d and has its tip or hooking portion hooked to an internal surface of securing portion 15d. Connection cable 71 will thus be secured to securing portion 15d of first cover 15 via cable holding member 72, and if connection cable 15 receives large force, connector 73 attached to the tip of connection cable 15 can be prevented from being detached from connector 33 assembled to populated board 31.

As shown in FIG. 3, illumination apparatus 1A having been assembled is generally a rectangular parallelepiped, and has an upper surface covered with transparent cover 60, a pair of longitudinally parallel side surfaces and a lower surface covered with chassis 10, and a pair of end surfaces orthogonal to the longitudinal direction covered with first cover 15 and second cover 16. Connection cable 71 is pulled out at a corner of illumination apparatus 1A that is generally a rectangular parallelepiped. As shown in FIG. 7, first cover 15 can have securing portion 15d biting into chassis 10 at a corner of chassis 10, and, as shown in FIG. 2, chassis 10 can have sidewall 12 with notch 18d to facilitate bending connection cable 71 in the longitudinal and widthwise directions of the casing. Furthermore, securing portion 15d provided at a corner of chassis 10 allows cable holding member 72 to be secured efficiently in terms of space.

As shown in FIG. 4, when transparent cover 60 is not attached, the casing has an upper side exposing holding member 40 and the plurality of lens 50, and the plurality of lenses 50 are aligned linearly in the longitudinal direction of the casing.

Figure 8:
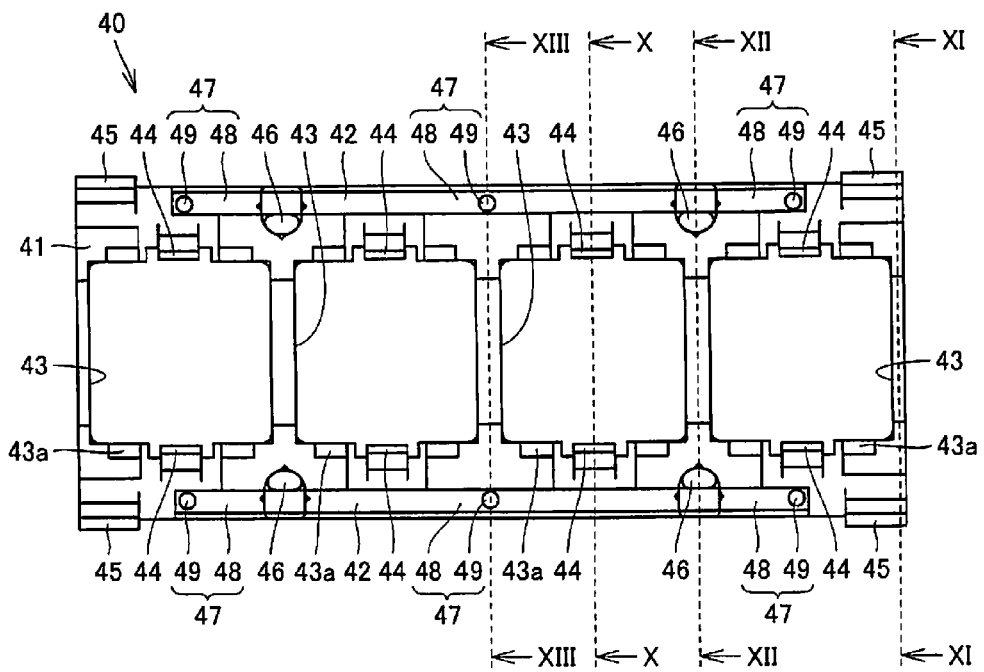
FIG. 8 is a bottom view of a holding member shown in FIG. 2 and FIG. 4.
Figure 9:
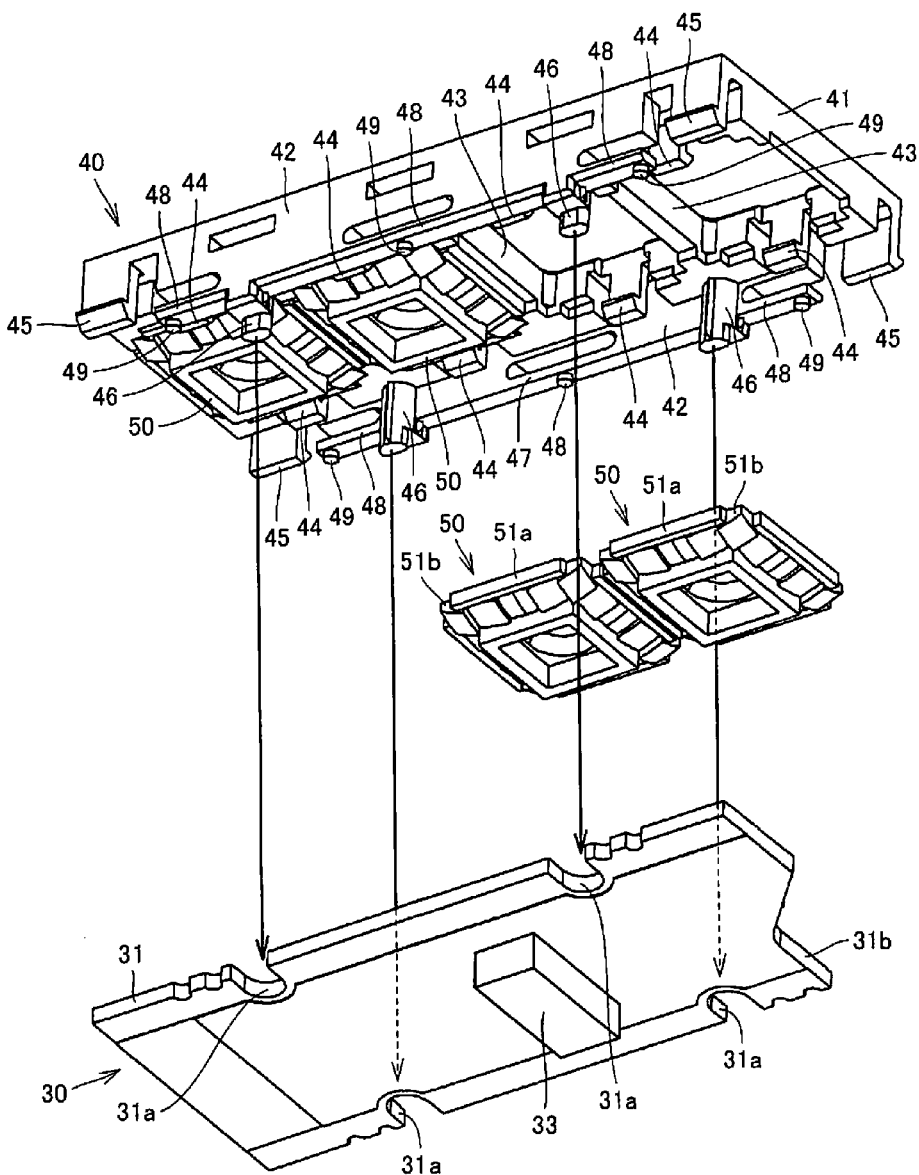
FIG. 9 is an exploded perspective view of a main portion for describing an assembly structure of the illumination apparatus in the first embodiment of the present invention.

FIG. 8 is a bottom view of the holding member shown in FIG. 2 and FIG. 4 and FIG. 9 is an exploded perspective view of a main portion for describing an assembly structure of the illumination apparatus in the present embodiment. Furthermore, FIG. 10 to FIG. 13 are schematic cross sections of the illumination apparatus taken along lines X-X, XI-XI, XII-XII, and XIII-XIII, respectively, shown in FIG. 8. Reference will be made to FIG. 8 to FIG. 13 to describe an assembly structure of illumination apparatus 1A in the present embodiment more specifically.

As shown in FIG. 8 and FIG. 9, the present embodiment provides illumination apparatus 1A such that holding member 40 is provided with various engagement mechanisms, positioning mechanisms, and the like. As described above, holding member 40 has base 41 having a plurality of openings 43 and a pair of side plate portions 42 erected from base 41 at a pair of opposite, longer-side ends, and base 41 and the pair of side plate portions 42 are provided with the various engagement mechanisms, positioning mechanisms, and the like.

Figure 10:
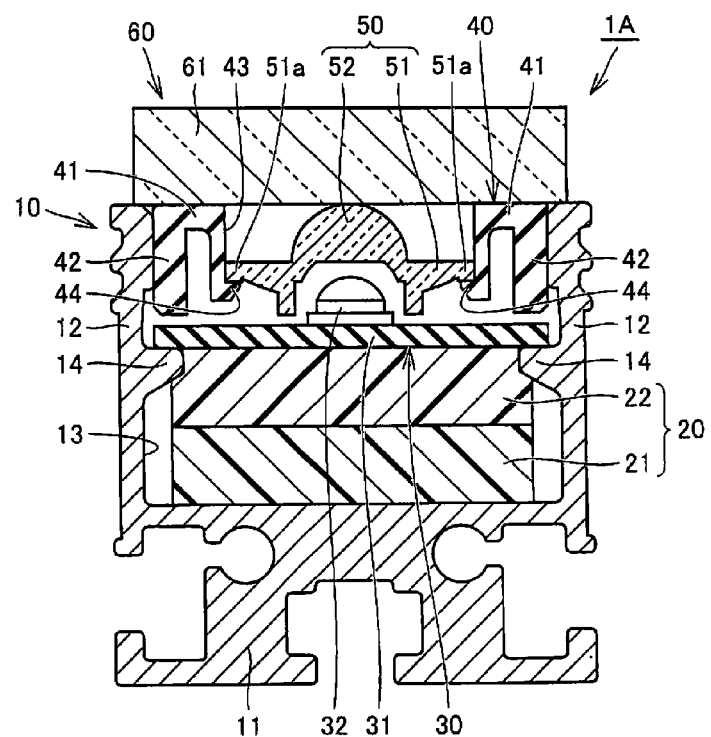
FIG. 10 is a schematic cross section of the illumination apparatus taken along a line X-X shown in FIG. 8.

As shown in FIG. 8 to FIG. 10, holding member 40 has base 41 with a lower surface (i.e., a major surface opposite to populated board 31 after it is assembled) provided with a recessed portion 43a along a perimeter of the plurality of openings 43 to receive a corner 51b of lens 50, and second hook 44 serving as a second engagement portion engaged with ear 51a of lens 50 to secure lens 50. Recessed portion 43a is provided to opening 43 at four corners, and second hook 44 is provided at a pair of opposite sides of opening 43 oppositely. Second hook 44 projects inwards.

As shown in FIG. 9, when lens 50 is assembled, it is inserted at the lower surface of holding member 40 into recessed portion 43a. In doing so, second hook 44 fits to ear 51a of lens 50 so that lens 50 is held by holding member 40 and thus fitted and secured thereto. Note that when lens 50 is fitted to and thus secured to holding member 40, a portion of lens 50, or corner 51b, will abut against a bottom surface of recessed portion 43a and this prevents lens 50 from detaching from an upper surface of holding member 40.

Figure 11:
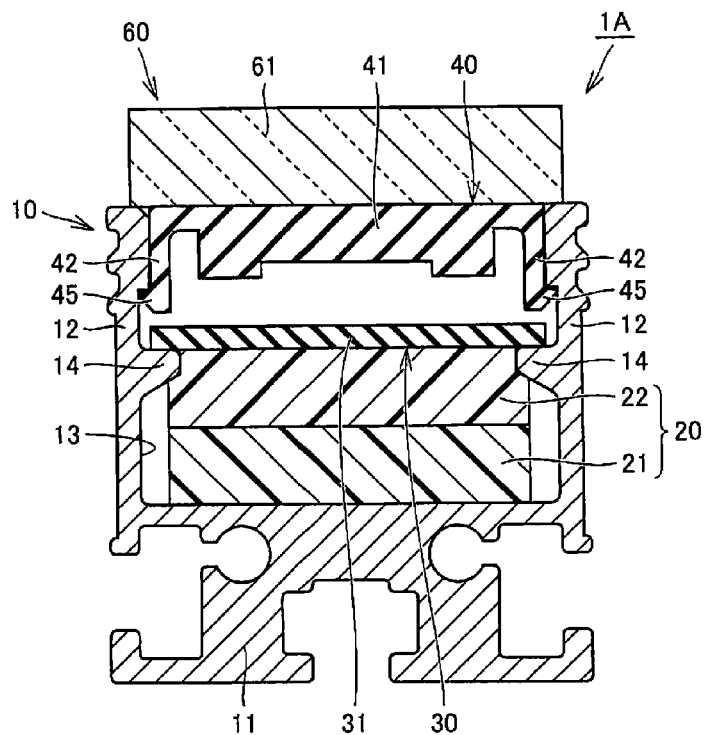
FIG. 11 is a schematic cross section of the illumination apparatus taken along a line XI-XI shown in FIG. 8.

As shown in FIG. 8, FIG. 9, and FIG. 11, holding member 40 has side plate portion 42 with a plurality of first hooks 45 at a prescribed position as a portion to be engaged. First hook 45 is a part for securing holding member 40 to chassis 10, and projects outward. When holding member 40 is assembled, it is inserted in housing portion 13 from the upper side of chassis 10, and in doing so, first hook 44 is fitted to a stepped surface (see FIG. 2 and FIG. 11), or first engagement portion 14b, of chassis 10 to fit holding member 40 in chassis 10 and thus secure the former to the latter.

Figure 12:
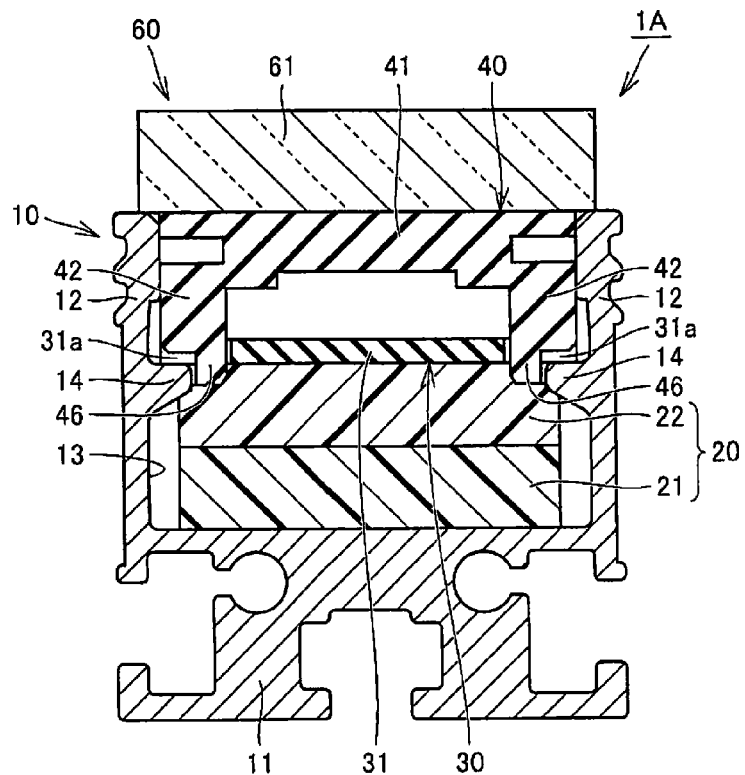
FIG. 12 is a schematic cross section of the illumination apparatus taken along a line XII-XII shown in FIG. 8.

As shown in FIG. 8, FIG. 9, and FIG. 12, holding member 40 has side plate portion 42 with a plurality of columns 46 at a prescribed position to project downward from a lower surface of side plate portion 42. Column 46 is provided to correspond to notch 31a of populated board 31, and is inserted into notch 31a when it is assembled.

Figure 13:
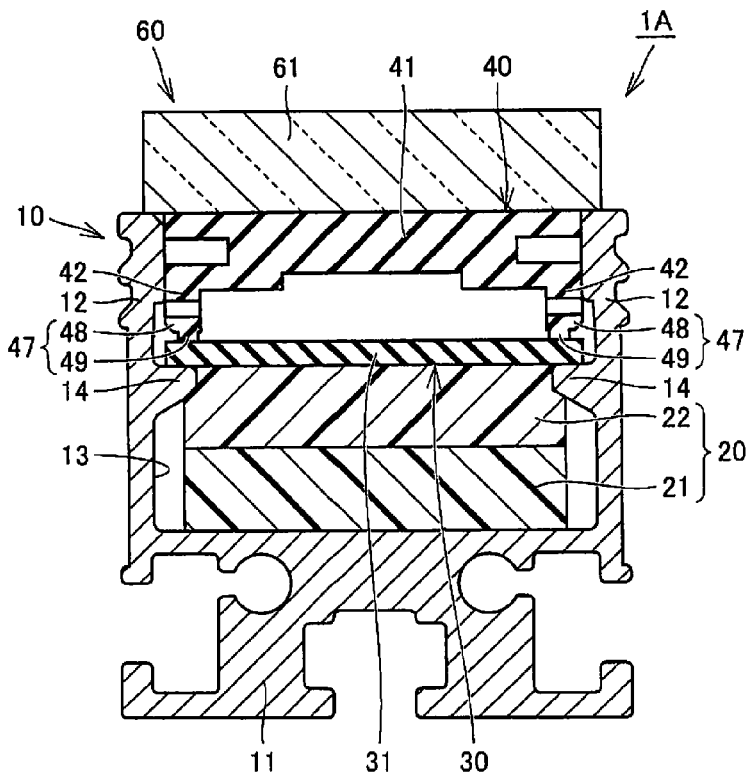
FIG. 13 is a schematic cross section of the illumination apparatus taken along a line XIII-XIII shown in FIG. 8.

As shown in FIG. 8, FIG. 9, and FIG. 13, holding member 40 has side plate portion 42 with a resilient biasing portion 47 at a prescribed position. Resilient biasing portion 47 is configured of a beam 48 extending in the longitudinal direction of holding member 40, and a projection 49 provided at a lower surface of beam 48, and is provided to side plate portion 42 at a lower end at a position different from that provided with column 46. Beam 48 is formed by providing a notch or an opening in side plate portion 42 at a prescribed position and thereby exhibits resilience. Preferably projection 49 is provided to beam 48 at the most deformable portion.

When holding member 40 and populated board 31 are assembled in chassis 10, resilient biasing portion 47 resiliently biases the longer-side ends of populated board 31 toward supporting portion 14a of chassis 10 (see FIG. 2 and FIG. 13). Herein, holding member 40 abuts against the front surface of populated board 31 only at a tip of projection 49 of resilient biasing portion 47, and thus biases populated board 31 toward supporting portion 14a and thus presses the former to the latter.

The assembly structure of illumination apparatus 1A described above is summarized with features as follows:

Chassis 10 includes bottom wall 11, a pair of sidewalls 12 erected from bottom wall 11 at a pair of opposite, longer-side ends, housing portion 13 defined by bottom wall 11 and the pair of sidewalls 12, a pair of supporting portions 14a projecting from the pair of sidewalls 12 toward housing portion 13 and supporting a pair of opposite, longer-side ends of populated board 31, and a pair of first engagement portions 14b provided at the pair of sidewalls 12 and fitting and securing holding member 40 to chassis 10. Housing portion 13 houses a plurality of light emitting devices 32, populated board 31, a plurality of lenses 50, holding member 40 and heat radiation member 20 therein.

Holding member 40 includes a plurality of openings 43 associated with the plurality of light emitting devices 32, second hook 44 serving as a plurality of second engagement portions fitting and securing the plurality of lenses 50 to holding member 40 in such a manner that the plurality of openings 43 are covered, and a plurality of resilient biasing portions 47 resiliently biasing the pair of longer-side ends of populated board 31 toward the pair of supporting portions 14a.

Populated board 31 is thus pinched and secured by the plurality of resilient biasing portions 47 and the pair of supporting portions 14a, and heat radiation member 20 is sandwiched and thus secured by populated board 31 and bottom wall 11 of chassis 10 in contact with populated board 31 and bottom wall 11.

Accordingly, if populated board 31 is warped, the holding member 40 resilient biasing portion 47 can exert resiliently biasing force to correct warpage of holding member 40 and thus allows lens portion 52 of lens 50 held by holding member 40 and light emitting device 32 mounted on board 31 to be positioned along the optical axis (i.e., the z axis) with precision, and a high-performance illumination apparatus can thus be provided.

Note that the holding member 40 resilient biasing portion 47 has resiliently biasing force generally much larger than that of the pair of highly thermally conductive sheets 21 and 22 serving as heat radiation member 20, and can thus correct the warpage of populated board 31 effectively. As its warpage is corrected, populated board 31 causes reaction force, which will be applied to resilient biasing portion 47 of holding member 40, and as holding member 40 having resilient biasing portion 47 and lens 50 are discrete members, lens 50 can be free of stress, and high reliability can thus be achieved.

Furthermore, the holding member 40 resilient biasing portion 47 exerts resiliently biasing force to press populated board 31 to supporting portion 14a of chassis 10 and thus secure populated board 31, and populated board 31 and bottom wall 11 of chassis 10 will sandwich heat radiation member 20. Heat radiation member 20, which compressively deforms, will closely contact the back surface of populated board 31 and bottom wall 11 of chassis 10 and can thus provide large radiation, and high reliability can also be achieved in this regard.

Furthermore, lens 50 and populated board 31 do not contact directly, and therebetween holding member 40 is interposed, and furthermore, holding member 40 and the front surface of populated board 31 contact only at the tip of projection 49, and this can significantly reduce the heat that is generated by the electronic components mounted on populated board 31 and is transferred to lens 50. This allows lens 50 to be also effectively free of thermal stress, and high reliability can also be achieved in this regard.

In addition, placing heat radiation member 20 and populated board 31 in housing portion 13 of chassis 10 and fitting in chassis 10 holding member 40 having the plurality of lens 50 fitted therein, that is, a simple operation allows a basic assembling operation to be completed, and significantly good assemblability can also be achieved.

Furthermore in the above assembly structure when holding member 40 is assembled it can have column 46 inserted into notch 31a of populated board 31 to also allow precise positioning in a plane parallel to the emission face (i.e., in the x-y plane) and the illumination apparatus can also be of high performance in this regard.

Thus the present embodiment provides illumination apparatus 1A that allows light emitting device 32 and lens portion 52 to be positioned with high precision, is excellent in assemblability, and is of high performance and significantly reliable.

Figure 14:
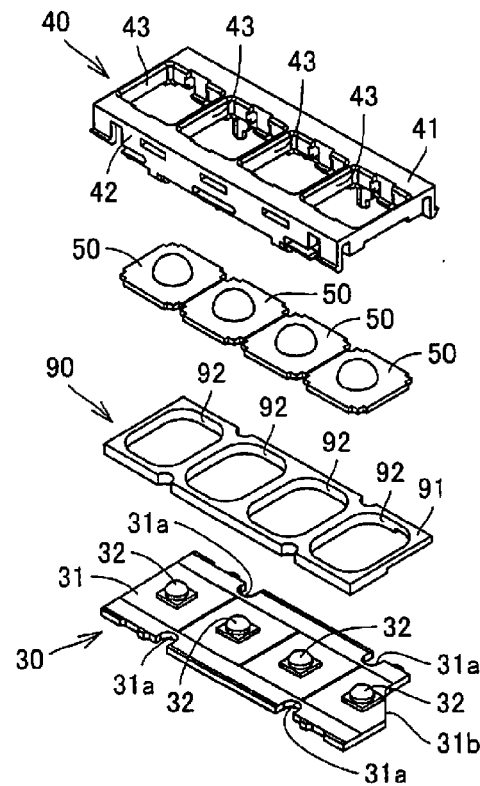
FIG. 14 is an exploded perspective view of the illumination apparatus in a first exemplary variation of the first embodiment of the present invention.
Figure 15:
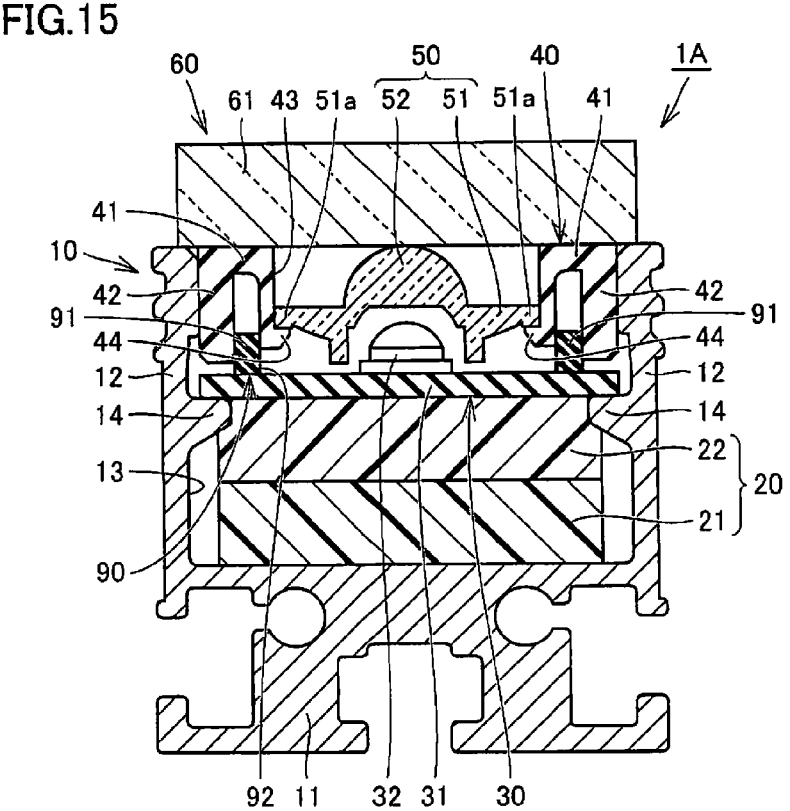
FIG. 15 is a schematic cross section of the illumination apparatus in the first exemplary variation of the first embodiment of the present invention.

FIG. 14 is an exploded perspective view of an illumination apparatus of the present embodiment in a first exemplary variation and FIG. 15 is a schematic cross section of the illumination apparatus in the first exemplary variation. With reference to FIG. 14 and FIG. 15, the illumination apparatus in the first exemplary variation will be described. Note that FIG. 14 only shows main components, and components that are not shown are similar to those in the present embodiment set forth above.

As shown in FIG. 14, the present variation provides an illumination apparatus equipped with a locking plate 90 to prevent lens 50 from dropping out of holding member 40 as holding member 40 has second hook 44 deformed for some reason. Locking plate 90 has a plurality of windows 92 associated with the plurality of lenses 50, and a frame 91 forming the plurality of windows 92. Locking plate 90 when assembled is disposed between populated board 31 and holding member 40.

As shown in FIG. 15, locking plate 90 has frame 91 pressed into a gap formed between second hook 44 and side plate portion 42 of holding member 40 having lens 50 fitted therein and thus secured thereto. Furthermore, as described above, locking plate 90 is disposed between populated board 31 and holding member 40, and accordingly, when locking plate 90 is assembled it will be located on populated board 31 and thus never be dropped from the gap.

Locking plate 90 thus has frame 91 introduced into the gap between second hook 44 and side plate portion 42, and accordingly, if lens 50 is pressed strongly towards light source unit 30, second hook 44 will not be deformed outwards (that is, in a direction opposite to lens 50) and can thus hold lens 50 steadily.

Figure 16:
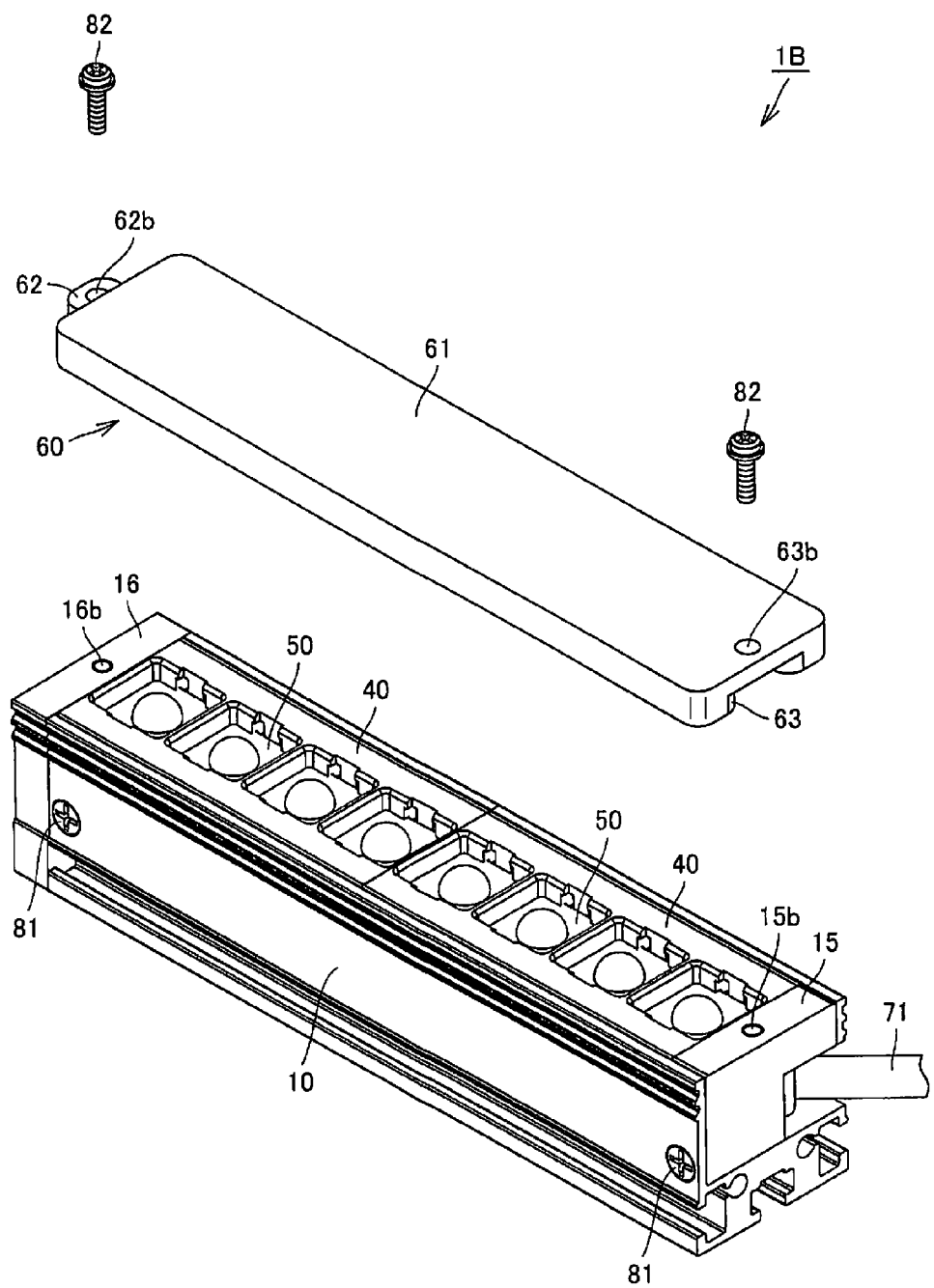
FIG. 16 is a partially exploded perspective view of the illumination apparatus in a second exemplary variation of the first embodiment of the present invention.

FIG. 16 is a partially exploded perspective view of an illumination apparatus of the present embodiment in a second exemplary variation. With reference to FIG. 16, the second exemplary variation provides an illumination apparatus 1B, as will be described hereinafter.

As shown in FIG. 16, the present variation provides illumination apparatus 1B different from of illumination apparatus 1A of the present embodiment described above in that chassis 10 and transparent cover 60 are further elongate members and that a plurality of elongate subassemblies each configured of a light source unit including a populated board and a light emitting device, holding member 40, and a plurality of lenses 50 are placed side by side in housing portion 13 of chassis 10 in the form of a single member in the longitudinal direction of chassis 10. Herein, the individual subassemblies are each similar to that in the present embodiment described above.

Previously preparing a plurality of chassis 10 and a plurality of transparent covers 60 different in length as variation allows additional light emitting devices to be introduced with standardized subassemblies used. This facilitates fabricating illumination apparatuses of different specifications.

Second Embodiment

Figure 17:
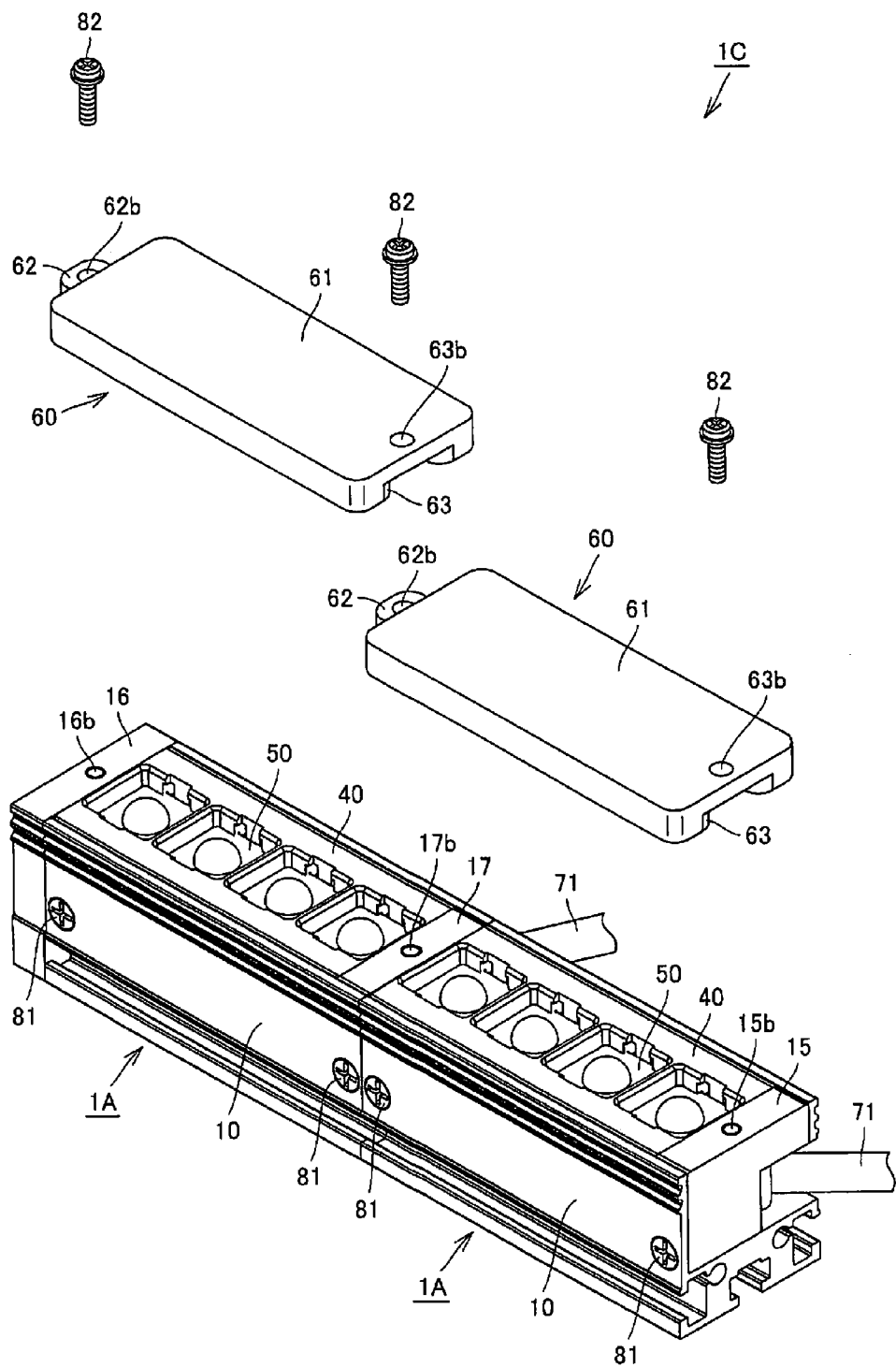
FIG. 17 is a partially exploded perspective view of an illumination system in a second embodiment of the present invention.

FIG. 17 is a partial exploded perspective view of an illumination system in a second embodiment of the present invention. With reference to FIG. 17, the present embodiment provides an illumination system 1C, as will be described hereinafter.

As shown in FIG. 17, the present embodiment provides illumination system 1C, which has illumination apparatus 1A coupled in the longitudinal direction to introduce additional light emitting devices. Note that the present embodiment provides illumination system 1C having illumination apparatus 1A coupled in a forward direction (that is, two illumination apparatuses 1A facing in the same direction and thus coupled together).

Specifically, in illumination system 1C, one illumination apparatus 1A has its second cover removed, the other illumination apparatus 1A has its first cover replaced with a third cover 17, as shown, used as a coupler to couple two illumination apparatuses 1A.

More specifically, third cover 17 has a portion inserted in the housing portion of the other illumination apparatus 1A and a portion inserted in the housing portion of one illumination apparatus 1A and these portions have side surfaces with screw holes, respectively, and screws 81 are screwed via screw holes of two chassis 10 into the screw holes of third cover 17 to secure two chassis 10. Two illumination apparatuses 1A are thus coupled together.

Furthermore, transparent cover 60 for one illumination apparatus 1A has projection 62 inserted into recessed portion 63 of transparent cover 60 for the other illumination apparatus 1A and projection 62 and recessed portion 63 have their respective screw holes 62b and 63b registered and in that condition two transparent covers 60 are placed over the casings. Then, screw holes 62b and 63b are further registered on a screw hole 17b provided in an upper surface of third cover 17, and screw 82 is screwed thereinto to assemble two transparent covers 60 to the casings.

This facilitates introducing additional light emitting devices and thus allows them to be introduced on site or the like. A user-friendly illumination apparatus and an illumination system including a plurality of such illumination apparatuses can thus be provided.

Third Embodiment

Figure 18:
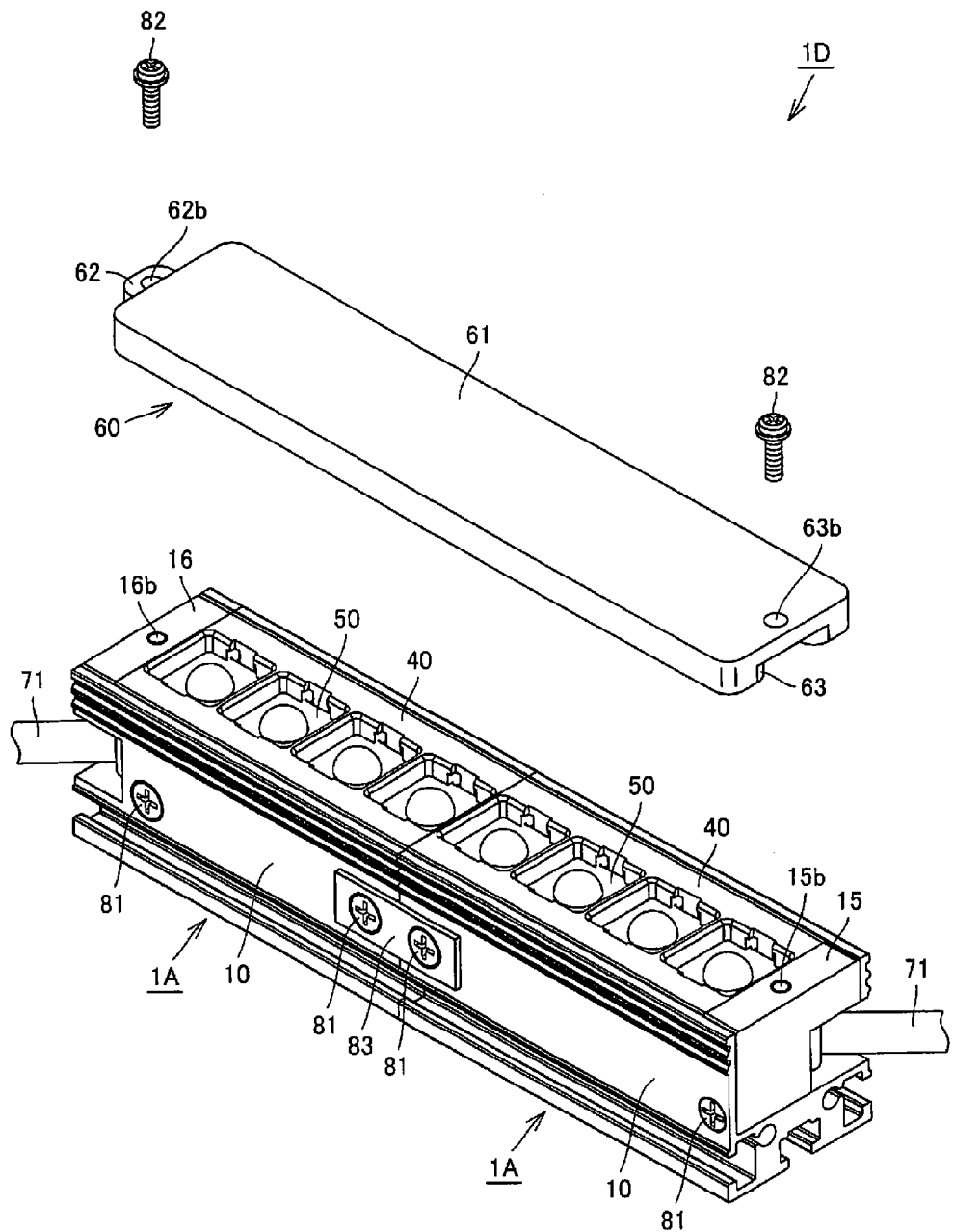
FIG. 18 is a partially exploded perspective view of an illumination system in a third embodiment of the present invention.

FIG. 18 is a partial exploded perspective view of an illumination system in a third embodiment of the present invention. With reference to FIG. 18, the present embodiment provides an illumination system 1D, as will be described hereinafter.

As shown in FIG. 18, the present embodiment provides illumination system 1D, which has illumination apparatus 1A coupled in the longitudinal direction to introduce additional light emitting devices. Note that the present embodiment provides illumination system 1C having illumination apparatus 1A coupled in a reverse direction (that is, two illumination apparatuses 1A directed differently from each other and thus coupled together).

Specifically, in illumination system 1D, one and the other illumination apparatuses 1A have their second covers removed and one illumination apparatus 1A having the second cover removed and the other illumination apparatus 1A having the second cover removed have their ends abutted against each other and in that condition a coupling member 83 as shown is used to secure two chassis 10. Two illumination apparatuses 1A are thus coupled together. Note that in this case, as shown, elongate transparent cover 60 previously prepared will be assembled to the casing.

This facilitates introducing additional light emitting devices and thus allows them to be introduced on site or the like. A user-friendly illumination apparatus and an illumination system including a plurality of such illumination apparatuses can thus be provided.

Figure 19:
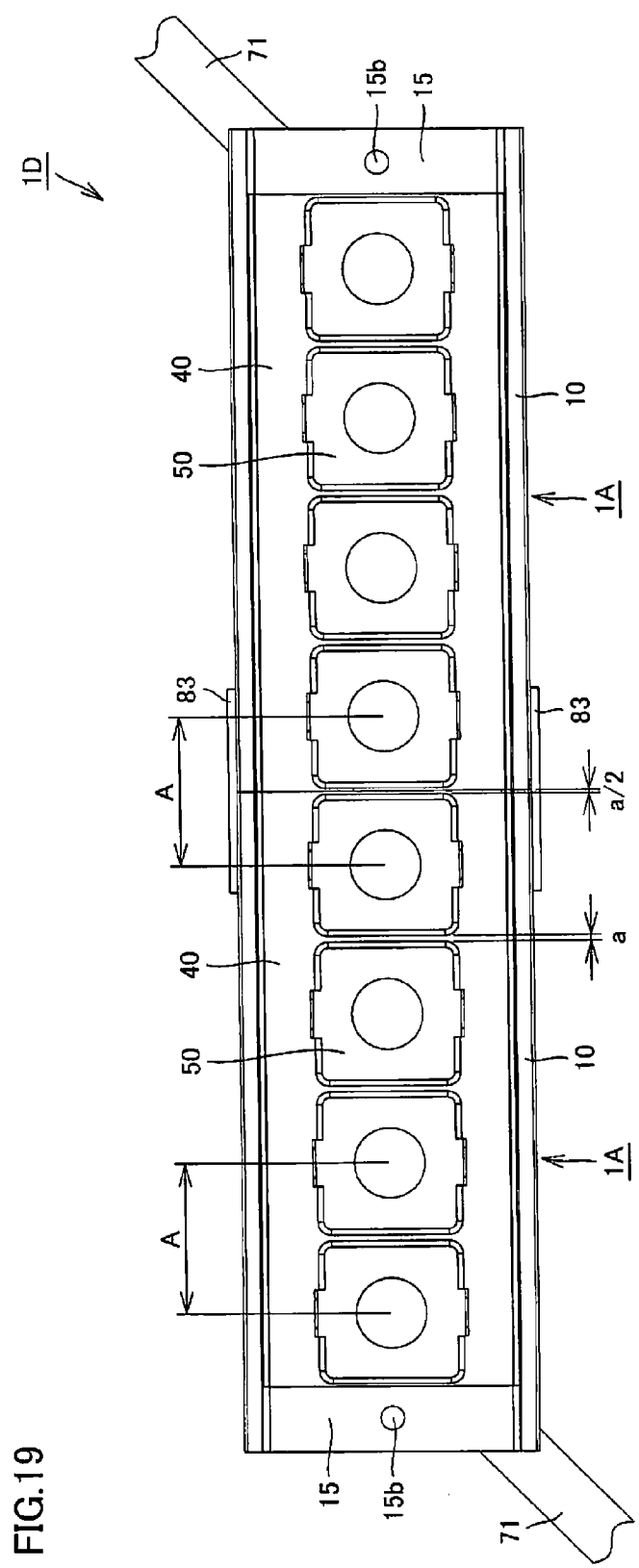
FIG. 19 is a plan view of the illumination system in the third embodiment of the present invention having a transparent cover removed.
Figure 20:
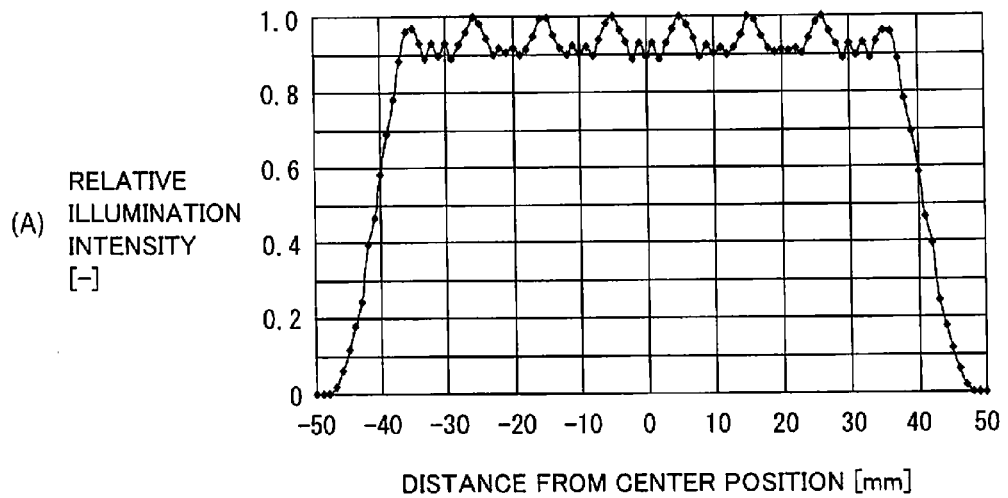
FIG. 20 plots the illumination system's illumination characteristics in the second and third embodiments of the present invention.
Figure 20:
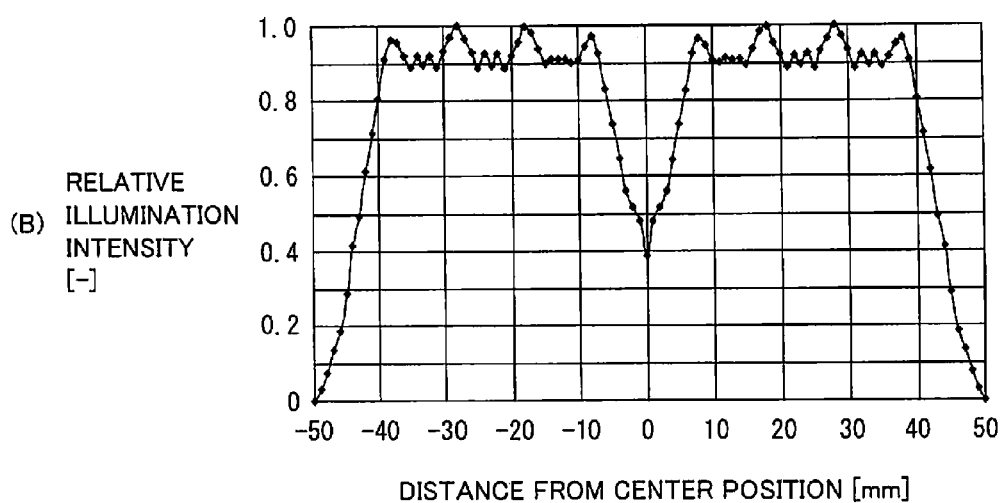

FIG. 19 is a plan view of the illumination system in the present embodiment having a transparent cover removed and FIG. 20 plots an illumination characteristic of the illumination system in the present embodiment and that of the illumination system in the second embodiment of the present invention for comparison in terms of illumination intensity. Note that FIG. 20 (A) plots how the present embodiment's illumination system varies in illumination intensity, as measured, and FIG. 20 (B) plots how the second embodiment's illumination system varies in illumination intensity, as measured.

The first embodiment's illumination apparatus 1A with holding member 40 modified in geometry allows an increased number of light emitting devices to be introduced without having an impaired illumination characteristic (variation in illumination intensity, in particular). Hereinafter, reference will be made to FIG. 19 and FIG. 20 to more specifically describe this point.

As has been described above, the first embodiment provides illumination apparatus 1A having light emitting devices, lenses, and openings aligned equally in pitch in the longitudinal direction of the chassis. Accordingly, when additional light emitting devices are introduced, they will successively be disposed equally in pitch and variation in illumination intensity can effectively be reduced/prevented.

Accordingly, in the present embodiment, as shown in FIG. 19, illumination apparatus 1A has holding member 40 with a plurality of openings 43, of which the opening closest to a longitudinal end of holding member 40 has a portion closest to the longitudinal end with a distance to the longitudinal end of ½ of a width a of a bar of holding member 40 located between immediately adjacent ones of openings 43. This allows holding members 40 to have their ends abutted against each other such that their respective openings 43 immediately adjacent to each other and each located at a longitudinal end of holding member 40 have a pitch equal to that of otherwise immediately adjacent openings 43, i.e., a pitch A, and uneven illumination can be prevented.

This is also clear from a test result shown in FIG. 20(A) and FIG. 20(B), and it has been confirmed that illumination system 1D in the present embodiment adjusted in, pitch as described above can significantly decreases uneven illumination, whereas illumination system 1C in an embodiment of the present invention described above that is not adjusted in pitch as described above provides significantly uneven illumination. Note that illumination apparatus 1B according to the exemplary variation based on the first embodiment of the present invention described above also has holding member 40 disposed in a structure basically similar to that in the present embodiment, and can thus achieve a similar effect.

While the present invention in the first to third embodiments and their exemplary variations provide light emitting devices linearly arranged in a line adjacently by way of example, the present invention is also applicable to light emitting devices aligned in a matrix, staggered, or aligned in other layouts. Furthermore, the present invention is not limited to four aligned light emitting devices as exemplified, and may have any plurality of light emitting devices.

Furthermore, while the present invention in the first to third embodiments and their exemplary variations provide a holding member and a casing, and a populated board with various engagement and positioning mechanisms each extending continuously in the longitudinal direction of the casing or provided intermittently by way of example, the engagement and positioning mechanisms' specific configurations, i.e., e.g., where, how many and in what geometry they are provided, may of course be modified as appropriate.

Furthermore while the present invention in the first to third embodiments and their exemplary variations allows additional light emitting devices to be introduced by coupling two holding members having equal numbers, respectively, of lenses by way of example, the additional light emitting devices may be introduced by coupling three or more holding members having equal numbers, respectively, of lenses, or coupling two or more holding members having different numbers, respectively, of lenses.

It should be understood that the embodiments and their variations disclosed herein are illustrative and non-restrictive in any respect. The scope of the present invention is defined by the terms of the claims, and is intended to include any modifications within the scope and meaning equivalent to the terms of the claims.

REFERENCE SIGNS LIST 1A, 1B: illumination apparatus; 1C, 1D: illumination system; 10: chassis; 11: bottom wall; 12: sidewall; 12a: screw hole; 13: housing portion; 14a: supporting portion; 14b: first engagement portion; 15: first cover; 15a, 15b: screw hole; 15d: securing portion; 16: second cover; 16a, 16b: screw hole; 17: third cover; 17b: screw hole; 18a, 18b, 18c, 19: groove; 18d: notch; 20: heat radiation member; 21, 22: highly thermally conductive sheet; 30: light source unit; 31: populated board; 31a, 31b: notch; 32: light emitting device; 33: connector; 40: holding member; 41: base; 42: side plate portion; 43: opening; 43a: recessed portion; 44: second hook; 45: first hook; 46: column; 47: resilient biasing portion; 48: beam; 49: projection; 50: lens; 51: base; 51a: ear; 51b: corner; 52: lens portion; 53: recessed portion; 54: reflection plane; 60: transparent cover; 61: diffusion plate portion; 62: projection; 62a: screw hole; 63: recessed portion; 63a: screw hole;

71: connection cable; 72: cable holding member; 72a: abutting portion; 72b: hook; 73: connector; 81, 82: screw; 83: coupling member; 90: locking member; 91: frame; 92: window; 100: image processing system; 110: camera; 120: strobe light controller; 130: image processor; 200: transport path; W: workpiece.

The invention claimed is:

1. An illumination apparatus comprising:
an elongate casing;
a plurality of light emitting devices serving as a light source;
a plurality of lenses disposed to correspond to said plurality of light emitting devices;
an elongate, populated board having a front surface and a back surface and populated at said front surface with said plurality of light emitting devices such that at least a portion of said plurality of light emitting devices are aligned in a longitudinal direction of said populated board;
a holding member disposed opposite to said front surface of said populated board and holding said plurality of lenses; and
a heat radiation member disposed along said populated board opposite to said back surface of said populated board, wherein:
said casing includes
a bottom wall,
a pair of sidewalls erected from a pair of opposite, longer-side ends of said bottom wall,
a housing portion defined by said bottom wall and said pair of sidewalls and receiving said plurality of light emitting devices, said populated board, said plurality of lenses, said holding member and said heat radiation member therein,
a pair of supporting portions projecting from said pair of sidewalls toward said housing portion and supporting a pair of opposite, longer-side ends of said populated board, and
a pair of first engagement portions provided at said pair of sidewalls and fitting and securing said holding member to said casing;
said holding member includes
a plurality of openings associated with said plurality of light emitting devices,
a plurality of second engagement portions fitting and securing said plurality of lenses to said holding member in such a manner that said plurality of openings are covered, and
a plurality of resilient biasing portions resiliently biasing said pair of longer-side ends of said populated board toward said pair of supporting portions; and
said plurality of resilient biasing portions and said pair of supporting portions pinch and thus secure said populated board, and said populated board and said bottom wall sandwich and thus secure said heat radiation member in contact with said populated board and said bottom wall.

2. The illumination apparatus according to claim 1, wherein:
said plurality of resilient biasing portions are each configured of a resiliently deformable beam and a projection provided on said beam at a major surface closer to said populated board; and
said projection has only a tip thereof abutting against said front surface of said populated board.

3. The illumination apparatus according to claim 1, wherein said plurality of second engagement portions fit and secure said plurality of lenses to said holding member such that said plurality of lenses each have a portion abutting against a surface of said holding member opposite to said populated board.

4. The illumination apparatus according to claim 1, wherein:
said holding member further includes a plurality of columns projecting toward said bottom wall;
said populated board includes a plurality of through holes associated with said plurality of columns and penetrating said populated board from said front surface to said back surface; and
said plurality of columns are inserted through said plurality of through holes.

5. The illumination apparatus according to claim 1, further comprising:
a connection cable having one end connected to said populated board and the other end pulled out of said casing and thus externally connected; and
a securing member for securing said connection cable to said casing, wherein:
said casing further includes a first closing member disposed at a position corresponding to one of a pair of opposite, shorter-side ends of said bottom wall to define said housing portion; and
said securing member is secured to said connection cable externally at a portion other than said ends and also fitted and secured to said first closing member.

6. The illumination apparatus according to claim 5, wherein said casing further includes a second closing member that is detachably attachable to a position corresponding to the other of said opposite, shorter-side ends of said bottom wall and defines said housing portion when said second closing member is attached to said position.

7. The illumination apparatus according to claim 1, wherein:
said plurality of light emitting devices, said plurality of lenses and said plurality of openings are all disposed in a longitudinal direction of said casing equally in pitch; and
of said plurality of openings, said opening closest to a longitudinal end of said holding member has a portion closest to said longitudinal end with a distance to said longitudinal end of ½ of a width of a bar of said holding member located between adjacent ones of said openings.

8. The illumination apparatus according to claim 1, wherein:
said plurality of light emitting devices, said plurality of lenses, said populated board and said holding member together configure an elongate subassembly; and
more than one said subassembly are disposed in said casing implemented as a single member such that said more than one said subassembly are aligned in a longitudinal direction of said casing.

9. An illumination system comprising more than one said illumination apparatus according to claim 1, said more than one said illumination apparatus being aligned in a longitudinal direction of said casing and mutually coupled and thus secured together.

* * * * *